(12) United States Patent
Wang et al.

(10) Patent No.: US 7,709,691 B2
(45) Date of Patent: *May 4, 2010

(54) PROCESS FOR GEOMETRIC ISOMERIZATION OF HALOGENATED OLEFINS

(75) Inventors: Haiyou Wang, Williamsville, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/499,509

(22) Filed: Jul. 8, 2009

(65) Prior Publication Data

US 2009/0270660 A1    Oct. 29, 2009

Related U.S. Application Data

(63) Continuation of application No. 11/588,466, filed on Oct. 27, 2006, now Pat. No. 7,563,936.

(51) Int. Cl.
*C07C 17/00*    (2006.01)
(52) U.S. Cl. .................................... 570/236
(58) Field of Classification Search .................. 570/236
See application file for complete search history.

(56) References Cited

U.S. PATENT DOCUMENTS

| 3,398,204 | A | 8/1968 | Gallant |
| 5,672,803 | A | 9/1997 | Smith et al. |
| 5,679,875 | A | 10/1997 | Aoyama et al. |
| 5,763,711 | A | 6/1998 | Ito |
| 5,986,151 | A | 11/1999 | Van Der Puy |
| 6,734,332 | B1 | 5/2004 | Slaugh et al. |
| 7,230,146 | B2 | 6/2007 | Merkel et al. |
| 7,420,094 | B2 | 9/2008 | Petrov et al. |
| 7,485,760 | B2 * | 2/2009 | Wang et al. .................. 570/236 |
| 7,534,366 | B2 | 5/2009 | Singh et al. |
| 7,592,494 | B2 * | 9/2009 | Tung et al. .................. 570/164 |
| 2004/0119047 | A1 | 6/2004 | Singh et al. |
| 2006/0269484 | A1 | 11/2006 | Knopeck et al. |

FOREIGN PATENT DOCUMENTS

| EP | 0752403 A2 | 1/1997 |
| GB | 880029 | 10/1961 |
| JP | 2000273058 A | 10/2000 |
| WO | 2005108334 A1 | 11/2005 |

OTHER PUBLICATIONS

Endo, Kiyoshi, et al., Monomer-Isomerization Polymerization-XXVI. The case of 2-Butene in the Presence of Isobutene with Ziegler-natta Catalyst, Eur. Polym. Journal, 1992, pp. 153-157, vol. 28, No. 2, Pergamon Press, Great Britain.

* cited by examiner

*Primary Examiner*—Jafar Parsa
(74) *Attorney, Agent, or Firm*—Bruce Bradford

(57) ABSTRACT

Disclosed are processes for the conversion of isomerizable halogenated C2-C6 olefins from one geometric form to a more preferred geometric form. Preferred process aspects comprise converting C2-C6 olefin in a cis-form to a trans-form comprising exposing the cis-form of the compound, preferably contained in process stream, to conditions effective to convert at least about 50 percent, and even more preferably at least about 70 percent, of the cis-form compound to the trans-form compound. Preferably the catalyst comprises at least one Lewis acid metal fluoride.

19 Claims, No Drawings

PROCESS FOR GEOMETRIC ISOMERIZATION OF HALOGENATED OLEFINS

CROSS REFERENCES TO RELATED APPLICATIONS

This application is a continuation application of U.S. application Ser. No. 11/588,466, filed Oct. 27, 2006, which is incorporated herein by reference.

FIELD OF THE INVENTION

The present invention relates to processes for the geometric isomerization of halogenated olefins. In certain aspects, the invention relates to processes for the conversion of cis-C2-C6 fluoroolefins to trans-C2-C6 fluoroolefins.

BACKGROUND OF THE INVENTION

Among the halogenated olefins, tetrafluoropropenes are known to be useful in numerous applications. For example, U.S. patent application Ser. No. 10/694,273, which is assigned to the assignee of the present invention and incorporated herein by reference, discloses the use of $CF_3CH=CFH$ as a refrigerant with low global warming potential and also as a blowing agent for use in connection with the formation of various types of foams. In addition, $CF_3CH=CFH$ can also be functionalized to variety of compounds useful as intermediates for making industrial chemicals.

Applicants have come to recognize, however, that certain geometric isomers of halogenated olefins are more preferred than others in certain embodiments. For example, the trans-form of tetrafluoropropene is more preferred in certain refrigerant applications than the cis-form. Applicants have also come to recognize that many of the current processes for producing halogenated olefins, and in particular tetrafluorinated propene, produce a mixture of the geometric isomers. As a result, applicants have discovered a need for processes which are capable of converting one geometric isomer of a halogenated olefin to a more desirable geometric isomer.

U.S. Pat. No. 6,734,332—Slaugh et al is directed to a method for enriching the concentration in a product stream of one geometric isomer relative to another. More specifically, this patent introduces a stream comprising a mixture of geometric olefinic isomers (cis- and trans-forms) into an adduct reaction zone where it is contacted with a linear polyaromatic compound which tends to preferentially bind to the desirable form of the geometric isomer. The adduct thus formed is thereafter readily separated from the less desirable geometric form, and subsequently the adduct is disassociated and separated to form a stream rich in the more desirable geometric form. One failure of this process, however, is that it does not have the advantage of producing further quantities of the desirable geometric form. Rather, this process involves substantial processing steps, and the associated costs thereof, to simply separate the existing geometric forms from one another.

U.S. Pat. No. 5,672,803 describes a method for selectively producing a trans-geometric isomer of non-conjugated diolefins. The process involves reacting an isomerizable non-conjugated diolefin with a combination of other olefinic compounds under catalytic conditions to selectively form the trans-non-conjugated diolefin isomer. The patent discloses that the preferred catalyst is rhenium, with tungsten, molybdenum, cobalt, tantalum, niobium and chromium been disclosed also as potential catalysts for the reaction. One drawback of this method, however, is that it is relatively complicated insofar as it requires that several molecular species are fed to the reaction system. This is a drawback not only from the standpoint of increasing the complexity of the process scheme, but also from the standpoint of raw material costs and subsequent separation equipment. In addition, the process disclosed in the U.S. Pat. No. 5,672,803 appears to be limited to isomerization of non-conjugated diene olefins.

The effectiveness of transition metal chlorides as isomerization catalysts was examined by K. Endo, S. Okayama and T. Otsu in connection with the monomer-isomerization polymerization of cis-2-butene. Applicants are unaware of any disclosed process for the cis- to trans-isomerization of halogenated C2-C6 olefins, and the present invention resides, at least in part, from the recognition of a need for such a process and the development of effective and efficient processes for performing such isomerization, particularly the conversion of cis-1,3,3,3-tetrafluoropropene to trans-1,3,3,3-tetrafluoropropene.

SUMMARY

Applicants have discovered a process for the conversion of isomerizable halogenated C2-C6 olefins from one geometric form to a more preferred geometric form.

Preferred process aspects of the invention involve converting C2-C6 olefin in a cis-form to a trans-form comprising exposing the cis-form of the compound, preferably contained in process stream, to conditions effective to convert at least about 50 percent, and even more preferably at least about 70 percent, of the cis-form compound to the trans-form compound. In preferred embodiments the C2-C6 olefin comprises tetrafluoropropene, with cis-1,3,3,3 tetrafluoropropene (cis-HFO-1234ze) being converted, preferably at high conversion rates and high selectivity, to trans-1,3,3,3 tetrafluoropropene (trans-HFO-1234ze). One important element of such preferred embodiments derives from the discovery by applicants that certain catalysts, when employed in accordance with the teachings contained herein are capable of effectively achieving such high conversion and selectivity levels for such reactions.

Thus, in preferred embodiments the conditions effective to achieve the desired high levels of conversion and selectivity include exposing the feed to a metal based catalyst selected from the group consisting of halogentated metal oxides, Lewis acid metal halides, zero-valent metals, and combinations of these, preferably under reaction conditions, including reaction temperature and residence time, effective to convert at least about 5% of the cis-form of the compound to other compounds and to further achieve a selectivity to the trans-form of the compound of at least about 70%.

DETAILED DESCRIPTION OF PREFERRED EMBODIMENTS

One aspect of the present invention provides processes, and catalyst compositions suitable for use in such processes, for isomerizing certain hydrocarbons, particularly hydrofluoroolefins, present in the cis-form of the molecule to the trans-form. More particularly, preferred embodiments of the present invention relate to the transformation of fluorinated olefin compounds having at least a first fluorine substituent and a second fluorine or fluorine-containing group (e.g., $CF_3$) cis- to one another across the olefin double bond and converting such a molecule to a form in which the first fluorine is located trans- to the second fluorine substituent or fluorine-containing group (e.g., CF$_3$) substituents are located trans- to one another. Although it is contemplated that the process and catalyst aspects of the present invention may be readily adapted for use in accordance with fluoroolefins generally, in preferred aspects the present methods and catalysts are adapted for use in connection with transformation of hydrofluoroolefins having three carbon compounds, and more particularly such three-carbon compounds having only fluorine substituents, and even more particularly namely tetrafluoropropenes.

It is contemplated that a wide variety of process streams may be utilized as the feed to the preferred reaction step of the present invention. For example, in certain embodiments of the present invention the feed stream which contains the cis-form of the compound to be converted may contain relatively low concentrations of this compound, for example less than about 50% by weight, or perhaps is even as little as 1% by weight. Generally, however, it is more preferred in many embodiments that the feed stream containing the cis-form of the compound to be converted in accordance with the present invention contains relatively high concentrations of the cis-molecule. Thus, in preferred embodiments, the feed stream in accordance with the preferred aspects of the present invention comprises at least about 5% by weight of the cis-form of the molecule, more preferably at least about 7% by weight, and even more preferably at least about 10% by weight of the cis-form of the molecule.

It is also contemplated that a wide variety of other molecules or materials which make up the balance of the feed stream to the reaction step of the present invention may be present in the feed stream without having a deleterious effect on the preferred conversion and selectivity features of the present invention. For example, it is contemplated that the feed stream to the reaction step of the present invention may originate as the effluent from an upstream process, as may exist, for example, in a commercial plant for producing fluorined olefins. In one contemplated embodiment of the present invention, the feed stream to the reaction step is the effluent, or at least a part of the effluent, from one or more upstream reactions which produce product stream(s) comprising un-reacted halogenated alkanes and cis-olefins, more particularly un-reacted fluorinated and/or chlorinated propanes and cis-form of fluorinated propenes. By way of more specific example, a patent application bearing application Ser. No. 11/588,464, which is being filed concurrently herewith and which is incorporated herein by reference, discloses a process including reacting one or more of the following fluorinated alkanes: chlorotetrafluoropropane (HCFC-244) and pentafluoropropane (HFC-245), including all isomers of each of these, but preferably 1-chloro, 1,3,3,3-tetrafluoropropane (HCFC-244fa), 1,1,1,3,3-pentafluoropropane (245fa), and 1,1,1,2,3-pentafluoropropane (245eb) to produce HFC-tetrafluoropropene. The reaction product frequently contains a proportion of un-reacted starting material and a combination of cis-1,3,3,3 tetrafluoropropene and trans-1,3,3,3 tetrafluoropropene, together with a hydrohalo compound, such as HF. One aspect of preferred embodiments of the present invention includes converting the cis-form of fluorinated olefin in such a stream and/or other similar streams which have been processed (by separation, for example) from this or similar reaction product streams to the trans-form, preferably at a conversion of at least about 1 percent, more preferably at least around 70%, and even more preferably at least about 90%, while at the same time preferably achieving a selectivity to the trans-form of the compound that is at least about 80%, even more preferably at least about 95%, and in certain highly preferred embodiments at least about 98%.

It is contemplated that the isomerization step may be preformed using a wide variety of process parameters and process conditions in view of the overall teachings contained herein, such as for example it is contemplated that the isomerization step may comprise, in certain nonpreferred embodiments, a liquid phase reaction. However, it is preferred in many embodiments of the present invention that this reaction step comprise a gas phase reaction, preferably in the presence of catalyst, preferably a metal catalyst.

Applicants have found that such highly desirable levels of cis- to trans-conversion and selectivity, and particularly and preferably from feed streams as described herein, by the proper selection of operating parameters, including, but not necessarily limited to, catalyst type, reaction temperature, and reaction residence time. Preferred aspects of each of these parameters are described below.

Applicants have found that three general types of catalysts are highly desirable and effective, when used in accordance with teachings contained herein, to achieve the aforesaid high level of conversion and selectivity. More specifically, preferred embodiments of the present processes generally comprise exposing the cis-form of the compound to a metal based catalyst selected from the group consisting of halogentated metal oxides, Lewis acid metal halides, zero-valent metals, and combinations of these.

With respect to catalysts comprising halogenated metal oxides and/or Lewis Acid metal halides, it is preferred that the metal component comprises, and preferably consists essentially of, one or more metals selected from transition metals, Boron group metals, rare earth metals, group VA metals, alkali metals, alkali earth metals, and combinations of these.

Although it is contemplated that many transition metals may be adaptable for use as the metal component in the catalysts of the present invention, it is generally preferred that the catalyst include a transition metal component selected from the group consisting of transition metals with an atomic number from about 21 to about 57 and transition metals having an atomic number of 77 (iridium) or 78 (platinum). For catalysts which have a metal component selected from the Boron group, such metals having an atomic number of from about 13 to about 81 are preferred, with Tl and Al being preferred from among these. For catalysts which have a metal component selected from the alkali earth metals, Mg is preferred. For catalysts which have a metal component selected from the Group VA metals. As used herein, reference to the periodic table is to the CAS version of the Periodic Table of Elements, with Sb preferred. For catalysts which have a metal component selected from among the alkali metals, those metals having an atomic number of from about 3 to about 37 are preferred, with those having an atomic number of from about 3 to about 19 being even more preferred. For catalysts which have a metal component selected from the rare earth metals, cerium is preferred. Of course it is contemplated that any and all combinations of the above-noted metal components, and other metal components not mentioned here, may be used in combination in accordance with the present invention.

For catalysts which are halogenated metal oxide catalysts (which are sometimes referred to herein for convenience as HMO catalysts) and Lewis Acid catalysts (which are sometimes referred to herein for convenience as LA catalysts), it is generally preferred that the catalysts include a transition metal or Al, and preferably when a transition metal is present it is selected from the group consisting of transition metals with an atomic number from about 21 to about 57, and combinations of these. From among the transition metals for use in HMO and LA catalysts, metals from Group VIB are preferred in certain embodiments, with Cr being especially preferred from among this group. In general for HMO and LA catalysts which include a transition metal component, the metal is preferably selected from the group consisting of Cr, Mo, V, Nb, Fe, La, Ni, Zn and combinations of these. In general for HMO and LA catalysts which include rare earth metal component, the metal is preferably Ce. In general for HMO and LA catalysts which include boron metal component, the metal is preferably selected from Al, Tl, and combinations of these. In general for HMO and LA catalysts which include an alkali earth metal component, the metal is preferably Mg. In general for HMO and LA catalysts which include alkali metal components, the metal is preferably selected from Li, Na, K and combinations of these.

It is contemplated that the metals used in the HMO catalysts and the LA catalysts of the present invention can be used in any available oxidation state. It is preferred in certain embodiments that the metals are used in accordance with the following oxidations states:

$Cr^{3+}$ and $Cr^{6+}$
$Mo^{6+}$
$V^{5+}$
$Nb^{5+}$
$Sb^{5+}$
$Ti^{4+}$
$Zr^{4+}$
$Ce^{4+}$
$Al^{3+}$
$Fe^{3+}$
$La^{3+}$
$Mg^{2+}$
$Ni^{2+}$
$Zn^{2+}$
$Li^{+}$
$Na^{+}$
$K^{+}$ In general, any halogen can be used as the component that is included in the HMO of the present invention. It is preferred, however, that the HMO catalyst of the present invention comprises a fluorinated metal oxide, more preferably a fluorinated transition metal oxide, and even more preferably fluorinated transition metal oxide wherein the metal is selected from the group consisting of Cr, Mo, V, Nb, Fe, La, Ni, Zn and combinations of these, fluorinated chromium oxide being highly preferred in certain embodiments. The agent and conditions used to treat the metal oxide to form the HMO catalyst can vary widely within the scope of the present invention. It is preferred in certain embodiments that the metal oxide be treated with one or more of the following halogenating agents: HF, $F_2$, HCl, $Cl_2$, HBr, $Br_2$, HI, $I_2$ and combinations of these. In certain highly preferred embodiments, the halogenating agent comprises one or more of HF, $F_2$, HCl, $Cl_2$, HBr, $Br_2$, and combinations of these, and even more preferably HF, $F_2$, HCl, $Cl_2F$ and combinations of these, and even more preferably HF, $F_2$, and combinations of these.

In general, any coordinating component can be used as the component that is included in the LA of the present invention. It is preferred, however, that the LA catalyst of the present invention comprises a Lewis Acid halide, more preferably a Lewis Acid halide in which the halogen component is selected from F, Cl, Br, I and combinations of these, more preferably F, Cl, Br and combinations of these, even more preferably F, Cl and combinations of these, and most preferably F. In certain highly preferred embodiments, the Lewis Acid catalyst is a Lewis Acid halide, preferably a fluoride, formed from a transition metal, and even more preferably a Lewis Acid halide formed from a transition metal selected from the group consisting of Cr, Mo, V, Nb, Fe, La, Ni, Zn and combinations of these, with Cr and Fe being preferred in certain embodiments. The agent and conditions used to form the LA catalyst can vary widely within the scope of the present invention. It is preferred in certain embodiments that the LA catalyst be formed, for example, by dissolving in an aqueous halogen salt, followed by evaporation and calcination. In one particular, but not limiting example, the process of forming the catalyst comprises: 1) dissolving quantities of metal hydroxides, oxides, and/or carbonates preferably, in aqueous HF solution (preferably separately in 49% aqueous HF solution), with mixing in a Teflon® container; 2) evaporation of the solution to dryness; 3) calcining the dried sample at an elevated temperature for a sufficiently long period, preferably in the presence of inert gas, such as $N_2$; and 4) optionally but preferably forming particles of the material so produced, preferably by grinding, to a fine powder, and then preferably by pelletizing into desired shapes.

With respect to neutral metal catalysts (which are sometimes referred to herein for convenience as NM catalysts), it is generally preferred that the catalysts include one or more transition metals selected from groups VIII and IB, with Co and Pd being preferred in certain embodiments.

The particular form of the catalyst can also vary widely. For example, the catalysts of this invention may contain other components, some of which may be considered to improve the activity and/or longevity of the catalyst composition. Preferred catalysts may in certain embodiments be promoted with compounds of molybdenum, vanadium, tungsten, silver, iron, potassium, cesium, rubidium, barium or combinations thereof. The catalyst may contain other additives such as binders and lubricants to help insure the physical integrity of the catalyst during granulating or shaping the catalyst into the desired form. Suitable additives include magnesium stearate, carbon and graphite. When binders and/or lubricants are added to the catalyst, they normally comprise about 0.1 to 5 weight percent of the weight of the catalyst. Furthermore, the catalyst may be used in a form where it is either unsupported or supported on a substrate, or in some cases a combination of these forms. It is contemplated that all types of supports known to those skilled in the art are useful in accordance with the present invention. By way of example, any of the catalysts mentioned herein may be supported on one or more materials, including but necessarily limited to the following: carbon; activated carbon; graphite; silica; alumina; fluorinated graphite; fluorinated alumina; and combinations of any two or more of these.

The catalyst may be activated prior to use by either HF treatment for HMO and LA catalysts or $H_2$ treatment for NM catalysts at elevated temperatures. After use for a period of time in the process of this invention, the activity of the catalyst may decrease. When this occurs, the catalyst may be reactivated. Reactivation of the catalyst may be accomplished by any means known in the art, for example, by passing air or oxygen diluted with nitrogen over the catalyst at temperatures of from about 100° C. to about 400° C., preferably from about 200° C. to about 375° C., for from about 0.5 hour to about 3 days, followed by either HF treatment at temperatures of from about 25° C. to about 400° C., preferably from about 200° C. to about 350° C., for HMO and LA catalysts or $H_2$ treatment at temperatures of from about 100° C. to about 400° C., preferably from about 200° C. to about 350° C., for NM catalysts.

It is also contemplated that the present processes, in view of the overall teachings contained herein, may be adaptable for use in accordance with a wide variety of reaction temperature conditions. For example it is contemplated that the reaction temperature in preferred embodiments may be from about 25° C. to about 600° C. As used herein, the term "reaction temperature" refers to the average temperature in the catalyst bed, unless otherwise indicated herein. In certain preferred embodiments, the reaction temperature is from about 50° C. to about 350° C., and even more preferably for about 75° C. to about 300° C.

Although a wide variety of temperatures is generally adaptable for use in connection with the present invention, applicants have surprisingly found that exceptional performance, in terms of conversion and/or selectivity, and preferably both, can be achieved by the use of reaction temperatures within the preferred range of from about 75° C. to about 350° C., more preferably from about 90° C. to about 250° C., and even more preferably from about 90° C. to about 110° C. While it is contemplated that these preferred ranges have application generally to conversion reactions in accordance with the present invention, such ranges produce in certain embodiments especially exceptional results, for example in connection with an isomerization of C2-C6 fluooolefins, more preferably C3-C4 fluoroolefins and even more preferably tetrafluorpropenes. Thus, for embodiments in which the isomerization reactions comprises, or preferably consists essentially of, converting cis-HFO-1234ze to trans-HFO-1234ze, it is preferred that the reaction temperature is from about 90° C. to about 250° C.

It is also contemplated that a wide variety of pressures may be used in connection with the processes of the present invention. Nevertheless, in certain preferred embodiments, the reaction is carried out under pressure conditions ranging from a vacuum of about 5 torr to about 200 psig.

It is also contemplated that a wide variety of contact times for the preferred reactions of the present invention may be used. Nevertheless, in certain preferred embodiments, the residence time is preferably from about 0.5 seconds to about 600 seconds.

In preferred aspects of the present invention, the cis-form of the compound to be converted is contained in a feed stream, and the converting step includes providing one or more reaction vessels, at least one of which preferably contains catalyst of the present invention and introducing the feed stream into the vessel(s) under conditions effective to achieve the desired conversion. It should be appreciated that the term "stream" as used herein is not limited to the singular, and it is contemplated that in certain embodiments separate streams are combined outside the vessel and then introduced to the vessel together, or in other embodiments separate streams might constitute the reactor feed, each of which is introduced into the vessel(s) at different times and/or at different locations. This same convention has been used and applied herein throughout to all use of the term "stream" herein, unless specifically indicated otherwise.

The following examples are given as specific illustrations of the invention. It should be noted, however, that the invention is not limited to the specific details set forth in the examples.

EXAMPLES

Example 1

Isomerization of Cis-1234ze over a Fluorinated $Cr_2O_3$ Catalyst

A catalyst (20 cc volume) of fluorinated $Cr_2O_3$ catalyst is used. A mixture of 85.3% cis-1234ze and 14.7% HFC-245fa is passed over this catalyst at a rate of 12 g/h at the temperatures indicated in Table 1 below. As shown in the Table, except at 30° C., the catalyst provided a cis-1234ze conversion above 80% and a trans-1234ze selectivity above 95% at all the temperatures investigated. These results indicate that the fluorinated $Cr_2O_3$ catalyst is very active and selective for converting cis-1234ze into trans-1234ze under the conditions of present invention.

TABLE 1

Isomerization of cis-1234ze over fluorinated $Cr_2O_3$ catalyst

| Reaction Temperature, C. | Conversion, % cis-1234ze | Selectivity, % trans-1234ze |
|---|---|---|
| 30 | 5.8 | 100 |
| 100 | 91.0 | 100 |
| 150 | 87.8 | 100 |
| 200 | 84.7 | 99 |
| 250 | 82.4 | 99 |
| 275 | 81.5 | 97.2 |

Example 2

Isomerization of Cis-1234ze over a Lewis Acid (Metal Halide) Catalyst

The catalysts used in this Example 2 include a series of unsupported and supported metal halides, namely, $AlF_3$, $FeF_3$, 10.0 wt % $FeCl_3$/AC, and 10.0 wt % LiCl/AC. 20 cc of each catalyst was used during reaction. A mixture of 85.3% cis-1234ze/14.7% 245fa was passed over each of the four catalysts at a rate of 12 g/h at a temperature ranged from 200 to 300° C. As shown in Table 2, at 200° C., the $AlF_3$ catalyst provided a cis-1234ze conversion of about 85% and a trans-1234ze selectivity of about 99%; at 300° C., the $FeF_3$ catalyst exhibited a cis-1234ze conversion of about 80% and a trans-1234ze selectivity of 100%. The $FeCl_3$/AC catalyst provided a conversion below 30% and a selectivity below 90%. These results indicate that metal fluoride catalysts are more active for the isomerization of cis-1234ze than the metal chloride ones.

TABLE 2

Isomerization of cis-1234ze over a Lewis Acid (metal halide) catalyst

| Catalyst | Reaction Temperature, C. | Conversion, % cis-1234ze | Selectivity, % trans-1234ze |
|---|---|---|---|
| $AlF_3$ | 200 | 85.2 | 99.3 |
| $FeF_3$ | 300 | 80.9 | 100 |
| 10.0 wt % $FeCl_3$/AC | 300 | 27.1 | 87.8 |
| 10.0 wt % LiCl/AC | 300 | 0.6 | 94.6 |

Example 3

Isomerization of Cis-1234ze over a Neutral Metal Catalyst

The catalysts used in Example 3 include two activated carbon supported Pd and Co catalysts, both of which have a 0.5 wt % metal loading. 20 cc of each catalyst was used during reaction. A mixture of 85.3% cis-1234ze/14.7% 245fa was passed over each of the two catalysts at a rate of 12 g/h at a temperature of 350° C. As shown in Table 3, both catalysts provided a cis-1234ze conversion of about 45% and a trans-1234ze selectivity of about 98%. These results indicate that the metallic palladium and cobalt catalysts show some activity for the transformation of cis-1234ze to trans-1234ze.

TABLE 3

Isomerization of cis-1234ze over a Neutral Metal catalyst

| Catalyst | Reaction Temperature, C. | Conversion, % cis-1234ze | Selectivity, % trans-1234ze |
| --- | --- | --- | --- |
| 0.5 wt % Pd/AC | 350 | 46.9 | 98.5 |
| 0.5 wt % Co/AC | 350 | 45.0 | 98.2 |

What is claimed is:

1. A process for the conversion of cis-1,3,3,3 tetrafluoropropene to trans-1,3,3,3 tetrafluoropropene comprising:
    a) providing a reactor feed comprising cis-1,3,3,3 tetrafluoropropene; and
    b) introducing said reactor feed to catalytic reaction conditions effective to convert at least a portion of said cis-1,3,3,3 tetrafluoropropene in said feed to trans-1,3,3,3 tetrafluoropropene, said conditions comprising exposing said feed, at a reaction temperature of from about 75 to about 350° C., to at least one Lewis acid metal fluoride.

2. The process of claim 1 wherein the metal component of said Lewis acid metal fluoride is selected from the group consisting of: (1) transition metals having an atomic number from about 21 to about 57; (2) metals from Group IIIA having an atomic number of from about 13 to about 81; (3) metals from Group VA having an atomic number of from about 51 to 83; (4) rare earth metals; (5) alkali metals from Group IA having an atomic number of from about 3 to about 37; (6) alkali metals from Group IIA having an atomic number of from about 12 to about 56; and (7) combinations of any two or more of them.

3. The process of claim 1 wherein the metal component of said Lewis acid metal fluoride is Al.

4. The process of claim 1 wherein the metal component of said Lewis acid metal fluoride is Fe.

5. The process of claim 1 wherein said reaction conditions are effective to convert at least about 5% of the cis-form and to achieve a selectivity to the trans-form of at least about 70%.

6. The process of claim 1 wherein said reactor feed comprises at least about 5% by weight of said cis-form.

7. The process of claim 1 wherein said reactor feed comprises at least about 5% by weight of said cis-form.

8. The process of claim 1 wherein said reactor feed is formed from at least a part of the effluent from one or more upstream reactions in a commercial process.

9. The process of claim 8 wherein said reactor feed comprises unreacted halogenated propanes and cis-form of fluorinated propenes.

10. The process of claim 1 wherein said reaction conditions are effective to convert at least about 70% of the cis-form and to achieve a selectivity to the trans-form of at least about 70%.

11. The process of claim 10 wherein said reaction conditions are effective to convert at least about 90% of the cis-form and to achieve a selectivity to the trans-form of at least about 80%.

12. The process of claim 10 wherein said reaction conditions are effective to convert at least about 95% of the cis-form and to achieve a selectivity to the trans-form of at least about 98%.

13. The process of claim 1 wherein said reaction temperature is from about 90 to about 250° C.

14. The process of claim 1 wherein said reaction temperature is about 200° C.

15. The process of claim 13 wherein said Lewis acid metal fluoride is aluminum fluoride.

16. The process of claim 14 wherein said Lewis acid metal fluoride is aluminum fluoride.

17. The process of claim 15 wherein said reaction conditions are effective to convert at least about 90% of the cis-form and to achieve a selectivity to the trans-form of at least about 80%.

18. The process of claim 15 wherein said reaction conditions are effective to convert at least about 95% of the cis-form and to achieve a selectivity to the trans-form of at least about 98%.

19. A process for the conversion of cis-1,3,3,3 tetrafluoropropene to trans-1,3,3,3 tetrafluoropropene comprising:
    a) providing a reactor feed comprising cis-1,3,3,3 tetrafluoropropene; and
    b) introducing said reactor feed to catalytic reaction conditions effective to convert at least a portion of said cis-1,3,3,3 tetrafluoropropene in said feed to trans-1,3,3,3 tetrafluoropropene, said conditions comprising exposing said feed, at a reaction temperature of about 200° C., to aluminum fluoride.

* * * * *